United States Patent
Migneco et al.

(10) Patent No.: US 11,173,818 B1
(45) Date of Patent: Nov. 16, 2021

(54) SEAT ASSEMBLY

(71) Applicant: Lear Corporation, Southfield, MI (US)

(72) Inventors: Francesco Migneco, Saline, MI (US); David Gallagher, Sterling Heights, MI (US)

(73) Assignee: Lear Corporation, Southfield, MI (US)

( * ) Notice: Subject to any disclaimer, the term of this patent is extended or adjusted under 35 U.S.C. 154(b) by 0 days.

(21) Appl. No.: 15/930,835

(22) Filed: May 13, 2020

(51) Int. Cl.
| | |
|---|---|
| *B60N 2/56* | (2006.01) |
| *A47C 7/72* | (2006.01) |
| *A47C 31/00* | (2006.01) |
| *A61B 5/18* | (2006.01) |
| *B60N 2/24* | (2006.01) |
| *B60N 2/90* | (2018.01) |
| *A61B 5/0205* | (2006.01) |

(52) U.S. Cl.
CPC .......... *B60N 2/5678* (2013.01); *A61B 5/0205* (2013.01); *B60N 2/914* (2018.02); *B60N 2/976* (2018.02); *B60N 2/99* (2018.02); *A61B 2562/0247* (2013.01)

(58) Field of Classification Search
CPC .. B60N 2/5657; B60N 2/5671; B60N 2/5678; B60N 2/976; B60N 2/5642; B60N 2002/0272; B60N 2/0232; A61B 5/0077; A61B 5/0205; A61B 5/02055
See application file for complete search history.

(56) References Cited

U.S. PATENT DOCUMENTS

| | | | |
|---|---|---|---|
| 5,769,490 | A | 6/1998 | Falzon |
| 6,056,360 | A | 5/2000 | Schneider |
| 6,079,485 | A | 6/2000 | Esaki et al. |
| 6,088,642 | A | 7/2000 | Finkelstein et al. |
| 6,088,643 | A | 7/2000 | Long et al. |
| 6,098,000 | A | 8/2000 | Long et al. |
| 6,179,378 | B1 | 1/2001 | Baumgartner et al. |
| 6,345,839 | B1 | 2/2002 | Kuboki et al. |

(Continued)

FOREIGN PATENT DOCUMENTS

| | | |
|---|---|---|
| CN | 2855822 Y | 1/2007 |
| CN | 203186154 U | 9/2013 |

(Continued)

OTHER PUBLICATIONS

Co-pending U.S. Appl. No. 16/821,128, filed Mar. 17, 2020.

(Continued)

*Primary Examiner* — Shin H Kim
(74) *Attorney, Agent, or Firm* — Fishman Stewart PLLC

(57) ABSTRACT

A seat assembly may include a seat including a seat base and a seat back, a sensor, a vent unit disposed at least partially within the seat back, and/or an electronic control unit (ECU) connected with the sensor and the vent unit. The ECU may be configured to determine, via the sensor, if a user of the seat exhibits symptoms of fatigue. The ECU may be configured to operate the vent unit in a first mode and a second mode. When the vent unit is in the first mode, the vent unit may provide cool air to said user of the seat. When the vent unit is in the second mode, the vent unit may provide warmer and/or less air to said user of the seat. The ECU may automatically switch the vent unit between first and second modes to reduce symptoms of fatigue.

20 Claims, 5 Drawing Sheets

(56) References Cited

U.S. PATENT DOCUMENTS

| | | |
|---|---|---|
| 6,353,207 B1 | 3/2002 | Burt |
| 6,506,153 B1 | 1/2003 | Littek et al. |
| 6,559,422 B2 | 5/2003 | Burt |
| 6,682,494 B1 | 1/2004 | Sleichter, III et al. |
| 6,908,152 B2 | 6/2005 | McMillen |
| 7,011,369 B2 | 3/2006 | Massara et al. |
| 7,083,232 B2 | 8/2006 | Frank |
| 7,083,233 B2 | 8/2006 | Massara et al. |
| 7,152,920 B2 | 12/2006 | Sugiyama et al. |
| 7,201,446 B2 | 4/2007 | Massara et al. |
| 7,219,923 B2 | 5/2007 | Fujita et al. |
| 7,267,652 B2 | 9/2007 | Coyle et al. |
| 7,303,231 B2 | 12/2007 | Frank |
| 7,314,451 B2 | 1/2008 | Halperin et al. |
| 7,417,536 B2 | 8/2008 | Lakshmanan et al. |
| 7,688,582 B2 | 3/2010 | Fukazu et al. |
| 7,731,279 B2 | 6/2010 | Asada et al. |
| 7,808,395 B2 | 10/2010 | Raisanen et al. |
| 7,828,050 B2 | 11/2010 | Esaki |
| 7,862,119 B2 | 1/2011 | Schafer et al. |
| 7,866,755 B2 | 1/2011 | Okano |
| 7,900,736 B2 | 3/2011 | Breed |
| 7,967,379 B2 | 6/2011 | Walters et al. |
| 7,967,381 B2 | 6/2011 | Sugiyama |
| 8,341,786 B2 | 1/2013 | Oexman et al. |
| 8,444,558 B2 | 5/2013 | Young et al. |
| 8,616,654 B2 | 12/2013 | Zenk et al. |
| 8,618,451 B2 | 12/2013 | Kunisada |
| 8,706,204 B2 | 4/2014 | Seo et al. |
| 8,710,784 B2 | 4/2014 | Meyer et al. |
| 8,725,311 B1 | 5/2014 | Breed |
| 8,794,707 B2 | 8/2014 | Bocsanyi et al. |
| 8,827,372 B2 | 9/2014 | Yoon |
| 8,958,955 B2 | 2/2015 | Hotary et al. |
| 8,971,839 B2 | 3/2015 | Hong |
| 8,979,191 B2 | 3/2015 | Friderich et al. |
| 8,989,697 B2 | 3/2015 | Leung et al. |
| 9,147,192 B2 | 9/2015 | Dawson et al. |
| 9,237,242 B2 | 1/2016 | Basir |
| 9,272,647 B2 * | 3/2016 | Gawade .............. B60N 2/5678 |
| 9,272,689 B2 | 3/2016 | Fung et al. |
| 9,277,385 B2 | 3/2016 | Iwamoto |
| 9,504,416 B2 | 11/2016 | Young et al. |
| 9,815,385 B2 | 11/2017 | Lippman et al. |
| 9,848,814 B2 | 12/2017 | Benson et al. |
| 9,883,821 B2 | 2/2018 | Muehlsteff |
| 9,978,283 B2 | 5/2018 | Jedrzejewski et al. |
| 9,980,680 B2 | 5/2018 | Matsumoto |
| 10,034,631 B1 | 7/2018 | Gallagher et al. |
| 10,210,409 B1 | 2/2019 | Migneco et al. |
| 10,213,147 B2 | 2/2019 | Gallagher et al. |
| 10,308,258 B2 | 6/2019 | Fung et al. |
| 10,328,823 B2 | 6/2019 | O'Bannon et al. |
| 10,358,065 B2 | 7/2019 | McMillen et al. |
| 10,369,074 B2 | 8/2019 | Oberg et al. |
| 10,379,535 B2 | 8/2019 | Migneco et al. |
| 10,391,900 B2 * | 8/2019 | Zhao ...................... B60N 2/58 |
| 10,470,968 B2 | 11/2019 | Saren et al. |
| 10,471,868 B2 | 11/2019 | Wheeler |
| 10,492,979 B2 | 12/2019 | Norman et al. |
| 10,556,532 B2 | 2/2020 | Gallagher et al. |
| 10,569,668 B2 | 2/2020 | Migneco et al. |
| 10,576,855 B2 | 3/2020 | Dorfler et al. |
| 10,640,010 B2 | 5/2020 | Yetukuri et al. |
| 10,709,386 B2 | 7/2020 | Gallagher et al. |
| 10,807,439 B2 | 10/2020 | Migneco et al. |
| 10,898,708 B2 * | 1/2021 | Franco-Obregon ...... A61N 2/02 |
| 2003/0039298 A1 | 2/2003 | Eriksson et al. |
| 2003/0075959 A1 | 4/2003 | Xue et al. |
| 2003/0209893 A1 | 11/2003 | Breed et al. |
| 2004/0119599 A1 | 6/2004 | Stevenson et al. |
| 2004/0129478 A1 | 7/2004 | Breed et al. |
| 2006/0244289 A1 | 11/2006 | Bedro |
| 2007/0118054 A1 | 5/2007 | Pinhas et al. |
| 2008/0161989 A1 | 7/2008 | Breed |
| 2008/0216567 A1 | 9/2008 | Breed |
| 2008/0255731 A1 | 10/2008 | Mita et al. |
| 2008/0267460 A1 | 10/2008 | Aoki et al. |
| 2008/0288406 A1 | 11/2008 | Seguin et al. |
| 2009/0008970 A1 | 1/2009 | Flory et al. |
| 2009/0030578 A1 | 1/2009 | Periot et al. |
| 2010/0087748 A1 | 4/2010 | Tobola et al. |
| 2011/0015468 A1 | 1/2011 | Aarts et al. |
| 2012/0080911 A1 * | 4/2012 | Brykalski .............. B60N 2/565 |
| | | 297/180.15 |
| 2012/0086249 A1 | 4/2012 | Hotary et al. |
| 2012/0089299 A1 | 4/2012 | Breed |
| 2012/0116149 A1 * | 5/2012 | Pilla ....................... A61N 2/006 |
| | | 600/14 |
| 2013/0090816 A1 | 4/2013 | Huber |
| 2013/0127210 A1 | 5/2013 | Jung et al. |
| 2013/0251216 A1 | 9/2013 | Smowton et al. |
| 2014/0070943 A1 * | 3/2014 | Breed ............... B60R 21/01516 |
| | | 340/539.11 |
| 2014/0132042 A1 | 5/2014 | Midderhoff et al. |
| 2014/0207333 A1 | 7/2014 | Vandivier et al. |
| 2014/0319895 A1 | 10/2014 | Lange-Mao et al. |
| 2014/0361871 A1 | 12/2014 | Silva et al. |
| 2014/0375089 A1 | 12/2014 | Qureshi et al. |
| 2015/0048658 A1 * | 2/2015 | Gawade ............... B60N 2/5678 |
| | | 297/180.12 |
| 2015/0084985 A1 | 3/2015 | Baudu |
| 2015/0266405 A1 | 9/2015 | Fitzpatrick et al. |
| 2015/0313475 A1 | 11/2015 | Benson et al. |
| 2015/0351692 A1 | 12/2015 | Pereny et al. |
| 2015/0352979 A1 | 12/2015 | O'Bannon et al. |
| 2015/0352990 A1 | 12/2015 | Zouzal et al. |
| 2015/0375653 A1 | 12/2015 | Josefsson et al. |
| 2016/0001781 A1 | 1/2016 | Fung et al. |
| 2016/0003882 A1 * | 1/2016 | Loftus .................. B60N 2/5685 |
| | | 324/750.11 |
| 2016/0143803 A1 | 5/2016 | Portales |
| 2016/0176409 A1 | 6/2016 | Kirsch et al. |
| 2016/0250956 A1 | 9/2016 | Seiting et al. |
| 2016/0278709 A1 | 9/2016 | Ridao Granado et al. |
| 2017/0043681 A1 | 2/2017 | Seiller et al. |
| 2017/0086588 A1 | 3/2017 | Patrick et al. |
| 2017/0225591 A1 | 8/2017 | Tobata et al. |
| 2017/0274906 A1 | 9/2017 | Hassan et al. |
| 2017/0349061 A1 | 12/2017 | Benson et al. |
| 2017/0361748 A1 | 12/2017 | Meachum et al. |
| 2018/0008507 A1 | 1/2018 | Saren et al. |
| 2018/0009343 A1 | 1/2018 | Saren et al. |
| 2018/0065642 A1 | 3/2018 | Frye et al. |
| 2018/0110960 A1 * | 4/2018 | Youngblood ........ A47C 27/085 |
| 2018/0178692 A1 * | 6/2018 | Zhao .................... B60N 2/5628 |
| 2018/0178808 A1 | 6/2018 | Zhao et al. |
| 2018/0215293 A1 | 8/2018 | Gandhi et al. |
| 2018/0325264 A1 | 11/2018 | Gallagher et al. |
| 2018/0345833 A1 | 12/2018 | Gallagher et al. |
| 2019/0053761 A1 | 2/2019 | Young et al. |
| 2019/0054796 A1 | 2/2019 | Thomas |
| 2019/0126036 A1 | 5/2019 | Franco-Obregon et al. |
| 2019/0133511 A1 | 5/2019 | Migneco et al. |
| 2019/0168771 A1 | 6/2019 | Migneco et al. |
| 2019/0193591 A1 | 6/2019 | Migneco et al. |
| 2019/0239815 A1 | 8/2019 | Gallagher et al. |
| 2019/0275860 A1 | 9/2019 | Migneco et al. |
| 2019/0332902 A1 | 10/2019 | Gallagher et al. |
| 2019/0337412 A1 | 11/2019 | Zouzal et al. |
| 2019/0337431 A1 | 11/2019 | McMillen et al. |
| 2019/0344043 A1 | 11/2019 | Migneco et al. |
| 2020/0035237 A1 | 1/2020 | Kim et al. |
| 2020/0113344 A1 * | 4/2020 | Youngblood ........ A61B 5/4815 |
| 2020/0170576 A1 | 6/2020 | Lerner |
| 2020/0188211 A1 | 6/2020 | Ellermann |
| 2020/0231428 A1 | 7/2020 | Migneco et al. |
| 2020/0253381 A1 | 8/2020 | Dorfler et al. |

(56) References Cited

U.S. PATENT DOCUMENTS

| | | | |
|---|---|---|---|
| 2020/0324675 A1 | 10/2020 | Yamamoto et al. |
| 2021/0016686 A1 | 1/2021 | Yetukuri et al. |

FOREIGN PATENT DOCUMENTS

| | | | |
|---|---|---|---|
| CN | 104252615 | A | 12/2014 |
| CN | 205468657 | U | 8/2016 |
| DE | 10027686 | A1 | 1/2002 |
| DE | 10063478 | A1 | 7/2002 |
| DE | 102004010626 | A1 | 6/2005 |
| DE | 102004013674 | A1 | 10/2005 |
| DE | 102006029871 | A1 | 1/2008 |
| DE | 102008029339 | A1 | 1/2009 |
| DE | 102009008421 | A1 | 10/2009 |
| DE | 102009035566 | A1 | 2/2010 |
| DE | 102009031331 | A1 | 8/2010 |
| DE | 102009033041 | A1 | 1/2011 |
| DE | 102010021332 | A1 | 1/2011 |
| DE | 102010049152 | A1 | 11/2011 |
| DE | 102011012431 | A1 | 11/2011 |
| DE | 102011016073 | A1 | 12/2011 |
| DE | 102011017238 | A1 | 12/2011 |
| DE | 102011102021 | A1 | 11/2012 |
| DE | 102011113100 | A1 | 3/2013 |
| DE | 102011116194 | A1 | 4/2013 |
| DE | 102012201430 | A1 | 4/2013 |
| DE | 102012216869 | A1 | 3/2014 |
| DE | 202015104103 | U1 | 8/2015 |
| DE | 102014002942 | A1 | 9/2015 |
| DE | 102015011460 | A1 | 3/2016 |
| DE | 102015011461 | A1 | 3/2016 |
| DE | 102017110812 | A1 | 1/2018 |
| DE | 102016011481 | A1 | 3/2018 |
| DE | 202017103162 | U1 | 5/2018 |
| DE | 102018000765 | A1 | 8/2019 |
| DE | 102018001230 | A1 | 8/2019 |
| DE | 202019100400 | U1 | 1/2020 |
| DE | 202019100710 | U1 | 2/2020 |
| DE | 102018007921 | A1 | 4/2020 |
| DE | 202019102879 | U1 | 5/2020 |
| DE | 202019105369 | U1 | 5/2020 |
| DE | 102019008724 | A1 | 8/2020 |
| EP | 1077154 | A2 | 2/2001 |
| EP | 1749477 | A1 | 2/2007 |
| EP | 1932715 | A1 | 6/2008 |
| EP | 2149475 | A1 | 2/2010 |
| EP | 2205460 | B1 | 3/2016 |
| FR | 2988654 | A1 | 10/2013 |
| GB | 2512136 | A | 9/2014 |
| JP | 2001269380 | A | 10/2001 |
| JP | 2005137896 | A | 6/2005 |
| JP | 2005237456 | A | 9/2005 |
| JP | 2006014756 | A | 1/2006 |
| JP | 3857869 | B2 | 12/2006 |
| JP | 2009172145 | A | 8/2009 |
| JP | 2012196253 | A | 10/2012 |
| JP | 2013163405 | A | 8/2013 |
| JP | 2019131049 | A | 8/2019 |
| WO | 2012/039368 | | 3/2012 |

OTHER PUBLICATIONS

Co-pending U.S. Appl. No. 15/930,777, filed May 13, 2020.
Co-pending U.S. Appl. No. 15/930,802, filed May 13, 2020.
Co-pending U.S. Appl. No. 15/930,865, filed May 13, 2020.
Co-pending U.S. Appl. No. 17/109,652, filed Dec. 2, 2020.

* cited by examiner

SEAT ASSEMBLY

TECHNICAL FIELD

The present disclosure generally relates to seat assemblies including seat assemblies that may be used in connection with automatically sensing and reducing fatigue.

BACKGROUND

This background description is set forth below for the purpose of providing context only. Therefore, any aspect of this background description, to the extent that it does not otherwise qualify as prior art, is neither expressly nor impliedly admitted as prior art against the instant disclosure.

Some seat assemblies may not when a user is experiencing fatigue. For example, some set assemblies may not be configured to reduce fatigue of a user by supplying cool air proximate a neck of a user.

There is a desire for solutions/options that minimize or eliminate one or more challenges or shortcomings of seat assemblies. The foregoing discussion is intended only to illustrate examples of the present field and is not a disavowal of scope.

SUMMARY

In embodiments, a seat assembly may include a seat including a seat base and a seat back, a sensor, a vent unit disposed at least partially within the seat back, and/or an electronic control unit (ECU) connected with the sensor and the vent unit. The ECU may be configured to determine, via the sensor, if a user of the seat exhibits symptoms of fatigue. The ECU may be configured to operate the vent unit in a first mode and a second mode. When the vent unit is in the first mode, the vent unit may provide cool air to said user of the seat. When the vent unit is in the second mode, the vent unit may provide a lesser amount of cool air and/or air at a higher temperature than the cool air to said user of the seat. The ECU may be configured to automatically switch the vent unit between the first mode and the second mode to reduce symptoms of fatigue of said user.

With embodiments, a seat assembly may include a seat including a seat base, a seat back, and a headrest, a bladder assembly disposed at least partially in the seat, a biomedical sensor configured to sense biomedical information of a user of the seat, an actuator assembly configured to control a position of the seat base and/or the seat back, a vent unit disposed at least partially within the seat back and including a portion disposed proximate the headrest, a PEMF coil assembly disposed at least partially in the seat back, and/or an ECU configured to control the actuator assembly, the bladder assembly, the vent unit, and the PEMF coil assembly. The biomedical sensor may be at least partially integrated with the bladder assembly. The ECU may be configured to determine, via the biomedical sensor, if a user of the seat exhibits symptoms of fatigue. The ECU may be configured to automatically operate the vent unit in a first mode and a second mode in an alternating configuration to reduce the fatigue symptoms of said user. When the vent unit is in the first mode, the vent unit may provide cool air to an area proximate a neck of said user. When the vent unit is in the second mode, the vent unit may provide a lesser amount of cool air and/or provides air at a higher temperature than the cool air. The ECU may be configured to automatically activate the actuator assembly, the bladder assembly, and/or the PEMF coil assembly when the vent unit is in the first mode to reduce the fatigue symptoms of said user.

In embodiments, a method of operating a seat assembly may include sensing, via the biometric sensor, if a user of the seat exhibits symptoms of fatigue, and/or automatically operating the vent unit in a first mode for a first duration and in a second mode for a second duration to reduce the symptoms of fatigue of said user. When the vent unit is in the first mode, the vent unit may supply cool air to said user. When the vent unit is in the second mode, the vent unit may provide a lesser amount of cool air and/or provides air at a higher temperature than the cool air.

The foregoing and other potential aspects, features, details, utilities, and/or advantages of examples/embodiments of the present disclosure will be apparent from reading the following description, and from reviewing the accompanying drawings.

BRIEF DESCRIPTION OF THE DRAWINGS

While the claims are not limited to a specific illustration, an appreciation of various aspects may be gained through a discussion of various examples. The drawings are not necessarily to scale, and certain features may be exaggerated or hidden to better illustrate and explain an innovative aspect of an example. Further, the exemplary illustrations described herein are not exhaustive or otherwise limiting, and are not restricted to the precise form and configuration shown in the drawings or disclosed in the following detailed description. Exemplary illustrations are described in detail by referring to the drawings as follows:

DETAILED DESCRIPTION

Reference will now be made in detail to embodiments of the present disclosure, examples of which are described herein and illustrated in the accompanying drawings. While the present disclosure will be described in conjunction with embodiments and/or examples, it will be understood that they do not limit the present disclosure to these embodiments and/or examples. On the contrary, the present disclosure covers alternatives, modifications, and equivalents.

Figure 1:
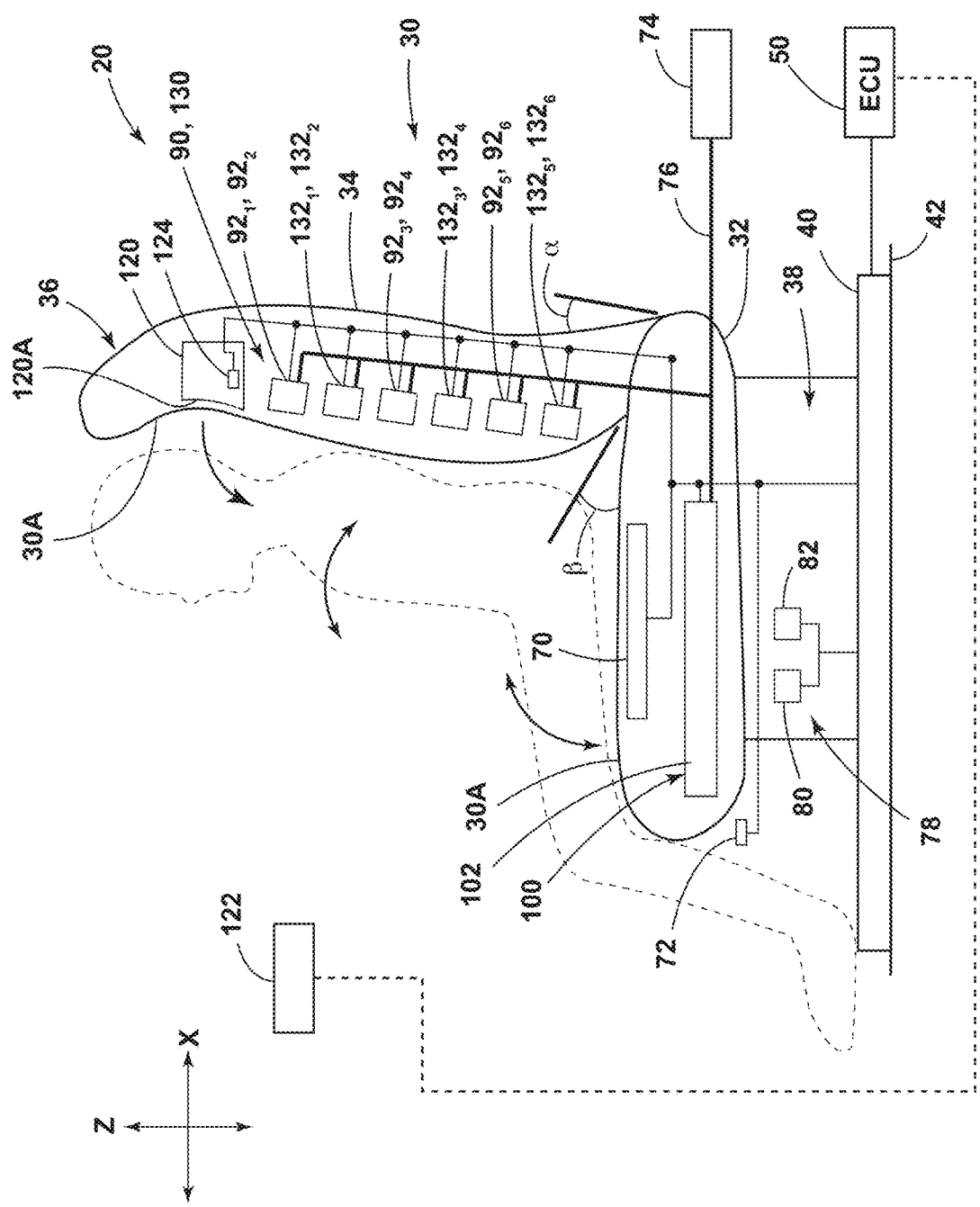
FIG. 1 is a side view generally illustrating an embodiment of a seat assembly according to teachings of the present disclosure.
Figure 2:
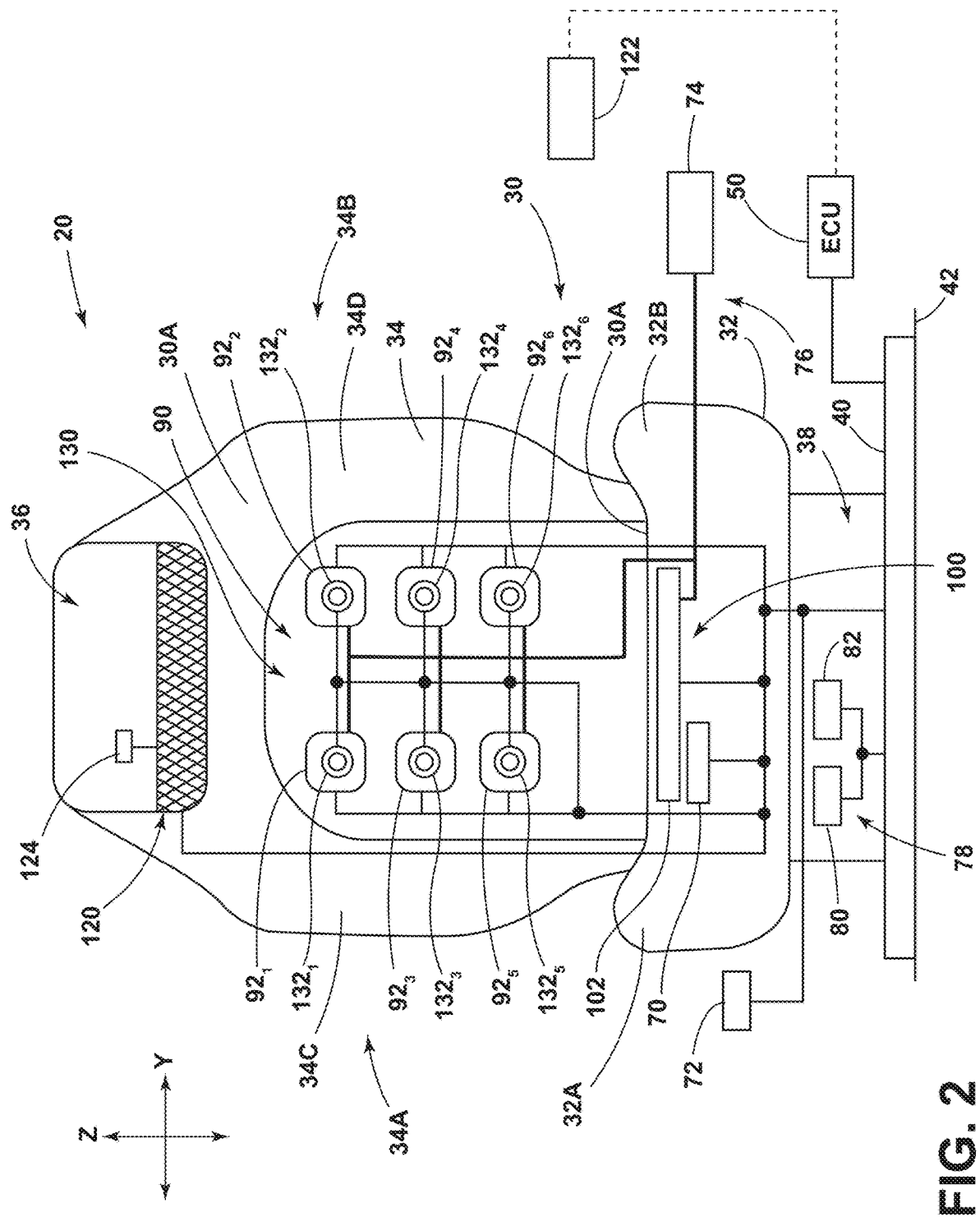
FIG. 2 is a front view generally illustrating portions of an embodiment of a seat assembly according to teachings of the present disclosure.

In embodiments, such as generally illustrated in FIGS. 1 and 2, a seat assembly 20 may include a seat 30, an electronic control unit (ECU) 50, a sensor 70, an actuator assembly 78 having a first actuator 80 and/or a second actuator 82, a first bladder assembly 90, a second bladder assembly 100, a vent unit 120, and/or a pulsed electromagnetic field (PEW') coil assembly 130. The ECU 50 may be connected with the seat 30, the sensor 70, the actuator assembly 78, the first bladder assembly 90, the second bladder assembly 100, the vent unit 120, and/or the PEMF coil assembly 130.

With embodiments, the ECU 50 may be configured to determine if a user (e.g., an occupant of the seat 30) exhibits signs/symptoms of fatigue, such as via the sensor 70 and/or a user interface 72. Symptoms of fatigue may, for example and without limitation, include large movements/fidgets by the user relative to the seat 30 that may be associated with long occupancy periods (e.g., vehicle trips of about 30 minutes or more). The ECU 50 may be configured to activate/control the first actuator 80, the second actuator 82, the first bladder assembly 90, the second bladder assembly 100, the vent unit 120, and/or the PEMF coil assembly 130, such as to reduce discomfort and/or reduce symptoms of fatigue of a user.

With embodiments, such as generally illustrated in FIGS. 1 and 2, a seat assembly 20 may include one or more seats 30. The seat 30 may include a seat base 32, a seat back 34, and/or a headrest 36. The seat 30 may be selectively connected (e.g., electrically and/or mechanically) to a track assembly 40. The ECU 50 may be configured to at least partially control operation of the seat 30. The ECU 50 may be electrically connected to the seat 30, such as via the track assembly 40. The seat 30 may be connected with the track assembly 40 via a support member 38. The support member 38 may be selectively connected with the track assembly 40. For example and without limitation, the support member 38 may be configured to be inserted vertically and/or horizontally into the track assembly 40. The support member 38 may be configured to be removed vertically and/or horizontally from the track assembly 40. The support member 38 may be configured to move along the track assembly 40 (e.g., in an X-direction and/or a Y-direction).

In embodiments, such as generally illustrated in FIGS. 1 and 2, a track assembly 40 may be disposed on and/or fixed to a mounting surface 42 (e.g., a vehicle floor). The track assembly 40 may be configured to receive the seat 30 substantially in an X-direction (e.g., a longitudinal direction) and/or a Z-direction (e.g., a vertical direction). The seat 30 and/or the support member 38 may be configured to be selectively inserted into and/or selectively removed from the track assembly 40 in one or more of a variety of locations along the track assembly 40 (e.g., one location, two locations, three or more locations, etc.). The track assembly 40 may, for example and without limitation, include one or more of variety of shapes, sizes, and/or configurations. The track assembly 40 may extend in an X-direction and/or a Y-direction (e.g., a transverse direction) such that the seat 30 may move in the X-direction and/or the Y-direction along the track assembly 40. With embodiments, a seat 30 may be connected to a mounting surface 42 independently of a track assembly 40 and/or a support member 38 (e.g., a seat assembly 20 may not include a track assembly 40).

Figure 3:
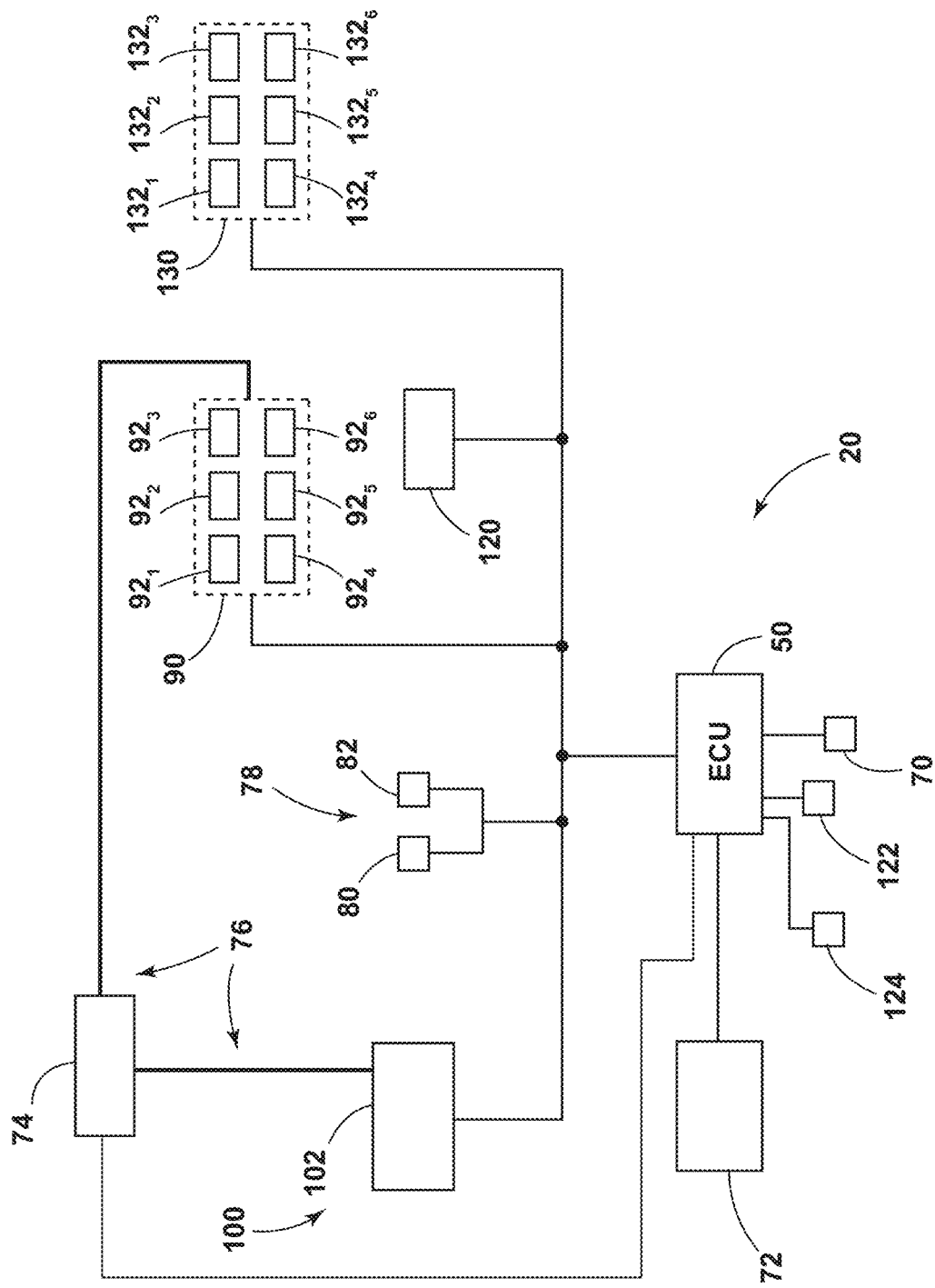
FIG. 3 is a schematic via generally illustrating portions of an embodiment of a seat assembly according to teachings of the present disclosure.

With embodiments, such as generally illustrated in FIGS. 1, 2, and 3, the seat assembly 20 may include one or more sensors 70. A sensor 70 may be configured to sense (e.g., measure, detect, obtain, monitor, etc.) biomedical and/or biometric information of the user occupying the seat 30, and the sensor 70 may be referred to herein as a biomedical sensor 70, but is not limited to a biomedical sensor. The sensor 70 may be configured to identify a user, and/or sense heart rate, breathing rate, blood pressure, fidgets/movements, and/or other information related to the user. For example and without limitation, the sensor 70 may include one or more cameras/visual devices, heart rate sensors, breathing rate sensors, blood pressure sensors, and/or fidget/ movement sensors (e.g., force/pressure sensors), among others. The sensor 70 may be disposed proximate the seat 30, such as in a vehicle cabin, in the seat base 32, and/or the seat back 34. The sensor 70 may be disposed substantially proximate a seating surface 30A of the seat 30, such as to increase the accuracy of sensed biomedical information. The sensor 70 may be configured to sense and/or obtain information associated with or indicating fatigue and/or discomfort of a user of/occupying the seat 30. Fatigue symptoms may, for example and without limitation, include increased or more significant movement/fidgeting, reduced or irregular heart rate, reduced or irregular heart rate variability, and/or reduced or irregular blood pressure (e.g., relative to baseline values/information that may be provided to and/or determined by the ECU 50), among others.

With embodiments, a sensor 70 may, for example and without limitation, include portions of and/or be integrated at least partially with the first bladder assembly 90 and/or the second bladder assembly 10. In some circumstances, the sensor 70 may include one or more pressure sensors connected to and/or integrated with the first bladder assembly 90 and/or the second bladder assembly 100. Changes in pressure in the bladder assemblies 90, 100 (and/or bladders thereof) may be sensed via the sensor 70 and may indicate that a user is fidgeting and/or is experiencing discomfort. The amount of a pressure change may correspond to the magnitude of the movement.

In embodiments, the ECU 50 may be electrically connected (e.g., via wired and/or wireless connection) with the sensor 70, such as to determine if the user exhibits signs of fatigue/discomfort. The ECU 50 may be configured to activate one or more seat functions, such as the first actuator 80, the second actuator 82, the first bladder assembly 90, the second bladder assembly 100, the vent unit 120, and/or the PEMF coil assembly 130, to reduce sensed fatigue symptoms/discomfort of the user. Additionally or alternatively, the user may manually activate the first actuator 80, the second actuator 82, the first bladder assembly 90, the second bladder assembly 100, the vent unit 120, and/or the PEMF coil assembly 130, such as via a user interface 72 (e.g., when the user desires to reduce symptoms of fatigue and/or discomfort). The user interface 72 may be configured to receive one or more of a variety of inputs (e.g., physical touch, audio, motion, etc.) from the user. For example and without limitation, at least a portion of the user interface 72 may be disposed substantially proximate the seat 30 such that the user may interact with the user interface 72 via physical touch.

In embodiments, the ECU 50 may be configured to monitor automatic and/or manual use of seat functions, such as the first actuator 80, the second actuator 82, the first bladder assembly 90, the second bladder assembly 100, the vent unit 120, and/or the PEMF coil assembly 130. The ECU 50 may, for example, monitor use of the seat assembly 20 to predict (via machine learning) when the user is likely to experience fatigue/discomfort during a trip. For example and without limitation, if a user has a history of manually activating one of more seat functions and/or exhibiting fatigue symptoms after a certain amount of time into trips, the ECU 50 may automatically activate one or more seat functions before that certain time. The ECU 50 may proactively activate functions of the seat assembly 20 to prevent and/or minimize user fatigue symptoms/discomfort.

With embodiments, such as generally illustrated in FIGS. 1, 2, and 3, an actuator assembly 78 of a seat assembly 20 may include a first actuator 80 that may be connected with the seat base 32 and/or may include a second actuator 82 that may be connected with the seat back 34. The first actuator 80 and/or the second actuator 82 may be connected to and/or disposed at least partially in the seat 30 and/or the support member 38. The first actuator 80 may be configured to actuate (e.g., rotate, shift, tilt, etc.) the seat base 32. The second actuator 82 may be configured to actuate the seat back 34. For example and without limitation, the first actuator 80 may be configured to rotate the seat base 32 in a first direction (e.g., clockwise in FIG. 1) and/or a second direction (e.g., counterclockwise in FIG. 1), such as about 90 degrees or more or less. The second actuator 82 may be configured to rotate the seat back 34 in a first direction (e.g., clockwise in FIG. 1) and/or a second direction (e.g., counterclockwise in FIG. 1), such as about 180 degrees, or more or less. The ECU 50 may be configured to control operation of the first actuator 80 and/or the second actuator 82. For example and without limitation, the first actuator 80 and/or the second actuator 82 may be electrically connected (e.g., via wired and/or wireless connection) with the ECU 50. The first actuator 80 and/or the second actuator 82 may be manually controlled by the user, such as via the user interface 72, and/or may be automatically controlled by the ECU 50 (e.g., for automatically preventing/reducing discomfort and/or fatigue symptoms).

In embodiments, such as generally illustrated in FIGS. 1, 2, and 3, a first bladder assembly 90 may include one or more bladders $92_N$ (e.g., fluid bladders). For example and without limitation, the first bladder assembly 90 may include a first bladder $92_1$, a second bladder $92_2$, a third bladder $92_3$, a fourth bladder $92_4$, a fifth bladder $92_5$, and/or a sixth bladder $92_6$. The first bladder assembly 90 may be disposed at least partially and/or substantially in the seat back 34. The first bladder $92_1$, the third bladder $92_3$, and/or the fifth bladder $92_5$ may be disposed substantially proximate a first side 34A of the seat back 34 (e.g., the left side in FIG. 2) and/or a first bolster 34C of the seat back 34. The second bladder $92_2$, the fourth bladder $92_4$, and/or the sixth bladder $92_6$ may be disposed substantially proximate a second side 34B of the seat back 34 (e.g., the right side in FIG. 2) and/or a second bolster 34D of the seat back 34. The first side 34A of the seat back 34 may be substantially opposite the second side 34B of the seat back 34. The first bladder $92_1$ and/or the second bladder $92_2$ may be disposed in the seat back 34 such that the first bladder $92_1$ and/or the second bladder $92_2$ may be generally proximate a shoulder area of the user. The third bladder $92_3$ and/or the fourth bladder $92_4$ may be disposed in the seat back 34 such that the third bladder $92_3$ and/or the fourth bladder $92_4$ may be generally proximate a thoracic area of the user (e.g., below the first and second bladders $92_1$, $92_2$). The fifth bladder $92_5$ and/or the sixth bladder $92_6$ may be disposed in the seat back 34 such that the fifth bladder $92_5$ and/or the sixth bladder $92_6$ may be generally proximate a lumbar area of the user (e.g., below the third and fourth bladders $92_3$, $92_4$).

With embodiments, the ECU 50 may be configured control operation (e.g., inflation/deflation) of the bladders $92_N$. For example and without limitation, the ECU 50 may be may be electrically connected (e.g., via wired and/or wireless connection) with the first bladder assembly 90 and/or a fluid source 74 that may be in fluid communication with the first bladder assembly 90, such as via one or more fluid conduits 76 (e.g., tubes, hoses, ducts, etc.). The fluid source 74 may, for example and without limitation, include a fluid pump, a fan, fluid reservoir, and/or one or more control valves, among other components, that may be configured to selectively provide fluid (e.g., air) to and/or remove fluid from the first bladder assembly 90 and/or the second bladder assembly 100. The ECU 50 may control the fluid source 74 to control the bladder assemblies 90, 100.

In embodiments, the ECU 50 may be configured to independently control operation of the first bladder $92_1$, the second bladder $92_2$, the third bladder $92_3$, the fourth bladder $92_4$, the fifth bladder $92_5$, and/or the sixth bladder $92_6$. The ECU 50 may inflate and/or deflate the first bladder assembly 90 such as to provide a massaging effect to the back of a user. The ECU 50 may be configured to inflate the bladders $92_N$ to one or more of a variety of pressures (e.g., that may be associated with a variety of massage pressure intensities). For example and without limitation, the ECU 50 may inflate the bladders $92_N$ to a first level of intensity and/or a second level of intensity. The first level of intensity of the bladders $92_N$ may correspond with a light massaging. The second level of intensity of the bladders $92_N$ may correspond to a pressure to warm up tissues in the back of the user. The second level of intensity of the bladders $92_N$ may apply a greater pressure to the back of a user than the first level of intensity of the bladders $92_N$.

In embodiments, the ECU 50 may be configured to automatically activate the first bladder assembly 90 upon determining that the user exhibits symptoms of fatigue/discomfort. For example and without limitation, the ECU 50 may determine that the user exhibits signs of fatigue/discomfort, such as via the sensor 70, and/or in response, the ECU 50 may automatically activate the first bladder $92_1$, the second bladder $92_2$, the fifth bladder $92_5$, and/or the sixth bladder $92_6$ at the first level and/or the second level. Additionally or alternatively, the user may manually activate the bladders $92_N$, such as via the user interface 72 that may be connected with the ECU 50 and/or the first bladder assembly 90. With some embodiments, the user may manually control inflation and/or deflation of respective bladders $92_N$ independently, such as to the first level and/or the second level via the user interface 72.

With embodiments, such as generally illustrated in FIGS. 1, 2, and 3, the second bladder assembly 100 may include one or more bladders. For example and without limitation, the second bladder assembly 100 may include one or more second assembly bladders 102. The second assembly bladders 102 may, for example, be disposed substantially in the seat base 32, such as at or about a bight line and/or at or about bolsters 32A, 32B of the seat base. The ECU 50 may control the second bladder assembly 100, such as via an electrical connection, and/or via a fluid source 74 that may be in fluid communication with the bladder 102. The ECU 50 may be configured to inflate and/or deflate the bladder 102, such as to adjust a position of the user while occupying the seat 30. Inflating and deflating the bladder 102 (e.g., adjusting the seating position of the user) may reduce fatigue/discomfort and/or fidgets exhibited by the user. The ECU 50 may inflate the bladder 102 to one or more of a variety of different pressures. For example and without limitation, the ECU 50 may (e.g., automatically) inflate the bladder 102 to a low pressure, a medium pressure, and/or a high pressure, such as according to a degree of fatigue/discomfort sensed via the sensor 70. The ECU 50 may inflate the bladder 102 to the low pressure to reduce a lesser degree of fatigue/discomfort, and/or the ECU 50 may inflate the bladder 102 to the high pressure to reduce a greater degree of fatigue/discomfort.

In embodiments, the ECU 50 may be configured to automatically activate the second bladder assembly 100 upon determining (e.g., via the sensor 70) that the user exhibits signs/symptoms of fatigue/discomfort. The ECU 50 may automatically inflate the second assembly bladder 102 to an appropriate pressure level (e.g., low pressure, medium pressure, and/or high pressure) to minimize one or more of a variety of fatigue levels of the user. Additionally or alternatively, the user may manually activate the bladder 102 (e.g. at a variety of pressures), such as via the user interface 72 that may be connected with the ECU 50 and/or the second bladder assembly 100.

With embodiments, such as generally illustrated in FIGS. 1, 2, and 3, a seat assembly 20 may include a vent unit 120. A vent unit 120 may, for example and without limitation, include an air conditioner, a fan, a pump, a heater, and/or one or more air ducts. The vent unit 120 may be configured to provide air substantially proximate an upper portion of the seat back 34 and/or substantially proximate the headrest 36, such as to provide air to a head, a neck, a shoulder area, and/or a torso of a user. The vent unit 120 may, for example and without limitation, be configured to move air from an area inside of the seat back 34 (and/or behind/below the seat back 34) to an area proximate a seating surface 30A of the seat back 34 (e.g., substantially proximate a head, neck, shoulders, and/or torso of the user). The vent unit 120 may be electrically connected (e.g., via wired and/or wireless connection) with the ECU 50, and/or the ECU 50 may be configured to control the vent unit 120. The ECU 50 may be configured to control the temperature of the air provided by the vent unit 120. The vent unit 120 may be configured to provide air at a plurality of temperatures. For example and without limitation, the vent unit 120 may be configured provide cool air (e.g., cooler than an ambient temperature) that may have a cool air temperature of about 15 degrees Celsius or less, and/or a cool air temperature about 7 degrees Celsius or more below an ambient temperature. A vent unit 120 may be disposed partially and/or substantially in the seat 30, such as in the seat back 34.

In embodiments, a seat assembly 20 may include one or more temperatures sensors, such as a first temperature sensor 122 and/or a second temperature sensor 124, that may be connected (e.g., via wired and/or wireless connection) to the ECU 50. The first temperature sensor 122 may be configured as an ambient temperature sensor and/or may be configured to obtain information relating to one or more ambient temperatures. The ambient temperature may include an exterior temperature (e.g., outside a vehicle) and/or an interior temperature (e.g., a vehicle interior/cabin temperature). The second temperature sensor 124 may be disposed proximate an outlet 120A of and/or at least partially within the vent unit 120. The ECU 50 may monitor the temperature of the air provided by the vent unit 120 via the second temperature sensor 124. For example and without limitation, the ECU 50 may utilize the second temperature sensor 124 to verify that the temperature of the air provided to the user is within a threshold range of a temperature that may be selected by the user (via the user interface 72) and/or the ECU 50.

With embodiments, the ECU 50 may be configured to control the vent unit 120 to provide cool air proximate an upper portion of the body of the user, such as to the ears, the neck, the shoulders, and/or the torso of the user. The ECU 50 may, for example and without limitation, provide cool air to the user to trigger a diving reflex of the user. Triggering a diving reflex involve lowering the temperature proximate the ears, head, neck, shoulders, and/or torso of the user, and may result in one or more physiological changes in the user, such as changes in heart rate, blood pressure, and/or breathing rate/pattern, among others. One or more of such physiological changes may generally tend to counter and/or reduce symptoms of fatigue, at least temporarily.

In embodiments, the ECU 50 may be configured to automatically activate the vent unit 120 upon sensing (e.g., via the sensor 70) that the user exhibits symptoms of fatigue/discomfort. Activating the vent unit 120 may include operating the vent unit 120 in a first mode and/or a second mode. When the ECU 50 operates the vent unit 120 in the first mode, the vent unit 120 may provide cool air to an upper portion of the user. When the ECU 50 operates the vent unit 120 in the second mode, the vent unit 120 may provide air that is warmer than the cool air provided in the first mode (e.g., may provide air at or about an ambient temperature) and/or may not provide a substantial amount of air to the user. The ECU 50 may operate the vent unit 120 in the first mode for a first duration, and/or may operate the vent unit 120 in the second mode for a second duration. For example and without limitation, the first duration may be about 4 minutes or more or less, and/or the second duration may be about 6 minutes or more or less. The ECU 50 may be configured to cycle the vent unit 120 between the first mode and/or the second mode for the first duration and/or the second duration, respectively, for a number of cycles (e.g., repeatedly). Switching from the first mode to the second mode may allow the user and/or air proximate the user to warm up so that when the vent unit 120 switches back to the first mode, the cool air is materially cooler than the user and/or the air proximate the user, which may facilitate triggering the diving reflex of the user again and/or may maximize fatigue symptom reduction via the vent unit 120. If the vent unit 120 is operated in the first mode for an extended period of time, the user may become accustomed to the cool air and/or the effects of triggering the diving reflex may taper off.

With embodiments, the ECU 50 may (e.g., automatically) cycle the vent unit 120 between the first mode and/or the second mode until the sensed biomedical information indicates that the user no longer exhibits or exhibits fewer/less severe symptoms of fatigue. Additionally or alternatively, the ECU 50 may prompt the user for input, such as via the user interface 72, to determine whether to maintain operation (e.g., cyclic operation) of the vent unit 120 or whether to deactivate the vent unit 120. The user may manually activate the vent unit 120 at one or more of a variety of temperatures and/or may override control of the vent unit 120 by the ECU 50 (at least temporarily), such as via the user interface 72, which may be connected with the ECU 50 and the vent unit 120.

In embodiments, such as generally illustrated in FIGS. 1, 2, and 3, a seat assembly 20 may include a PEMF coil assembly 130. The PEMF coil assembly 130 may include one or more PEMF coils $132_N$. For example and without limitation, the PEMF coil assembly 130 may include a first coil $132_1$, a second coil $132_2$, a third coil $132_3$, a fourth coil $132_4$, a fifth coil $132_5$, and/or a sixth coil $132_6$. The coils $132_N$ may be disposed in the seat back 34. The coils $132_N$ may be disposed in one or more locations within the seat back 34. For example and without limitation, such as generally shown in FIG. 1, the coils $132_N$ may be disposed substantially proximate the bladders $92_N$ of the first bladder assembly 90. With embodiments, such as generally illustrated in FIG. 2, the coils $132_N$ may be disposed at least partially within the bladders $92_N$ of the first bladder assembly 90. For example and without limitation, the first coil $132_1$ may be disposed at least partially in the first bladder $92_1$, the second coil $132_2$ may be disposed at least partially in the second bladder $92_2$, the third coil $132_3$ may be disposed at least partially in the third bladder $92_3$, the fourth coil $132_4$ may be disposed at least partially in the fourth bladder $92_4$, the fifth coil $132_5$ may be disposed at least partially in the fifth bladder $92_5$, and/or the sixth coil $132_6$ may be disposed at least partially in the sixth bladder $92_6$. The PEMF coil assembly 130 may be electrically connected (e.g., via wired and/or wireless connection) with the ECU 50 such that the ECU 50 may activate and/or deactivate the coils $132_N$ of the PEMF coil assembly 130 (e.g., independently).

With embodiments, the ECU 50 may activate one or more coils $132_N$ to reduce fatigue symptoms and/or discomfort, such as fatigue symptoms and/or discomfort that may be associated with osteo-articular pain and/or inflammation. The ECU 50 may independently control operation of the coils $132_N$ to apply PEMF therapy to specific areas of the user. For example and without limitation, the ECU 50 may operate the first coil $132_1$ and/or the second coil $132_2$ to provide PEMF therapy substantially proximate a neck/shoulder area of the user. The ECU 50 may operate the third coil $132_3$ and/or the fourth coil $132_4$ to provide PEMF therapy substantially proximate a thoracic area of the user. The ECU 50 may operate the fifth coil $132_5$ and/or the sixth coil $132_6$ to provide PEMF therapy substantially proximate a lumbar area of the user.

In embodiments, the ECU 50 may be configured to automatically activate the PEMF coil assembly 130 upon sensing that the user is experiencing fatigue symptoms and/or discomfort (e.g., via the sensor 70). Additionally or alternatively, the user may manually activate the coils $132_N$ of the PEMF coil assembly 130, such as via the user interface 72, which may be connected with the ECU 50 and/or the PEMF coil assembly 130. The user may, for example, operate the coils $132_N$ individually to address targeted areas of inflammation and/or osteo-articular pain.

In embodiments, the ECU 50 may determine if the user of the seat 30 is a driver/pilot of a vehicle (e.g., if the seat 30 is disposed in a vehicle, whether the seat 30 is a driver seat), such as according to user input via the user interface 72, and/or whether the user is experiencing fatigue symptoms and/or discomfort. If the ECU 50 determines that user is the driver, the ECU 50 may be configured to activate the first bladder assembly 90, the second bladder assembly 100, the vent unit 120, and/or the PEMF coil assembly 130 to reduce fatigue symptoms and/or discomfort.

With embodiments, the ECU 50 may be configured to determine if the seat 30 is not occupied by a driver (e.g., is not a driver seat) and/or the ECU 50 may be configured to operate functions of a seat 30 differently if the user associated with the seat is not a driver. For example and without limitation, the ECU 50 may suggest activating one or more seat functions to the user, and may suggest not triggering the vent unit 120 to non-driving users if such users are trying to rest/sleep. In some circumstances, the ECU 50 may be configured not to activate the first actuator 80 and/or the second actuator 82 if doing so would interfere with the driving ability of the driver. Additionally and alternatively, if the seat base 32 and/or the seat back 34 are not able to be actuated (e.g., if actuating the seat base 32 and/or the seat back 34 may cause contact with another seat, cargo, and/or other user), the ECU 50 may activate the second bladder assembly 100 to reposition the user as an alternative to repositioning the user via the first actuator 80 and/or the second actuator 82.

With embodiments, such as generally illustrated in FIG. 6, a method 170 of operating a seat assembly 20 may include providing a seat 30, an ECU 50, a sensor 70, an actuator assembly 78, a first bladder assembly 90, a second bladder assembly 100, a vent unit 120, and/or a PEMF coil assembly 130 (step 172). The ECU 50 may be connected to and/or configured to control the sensor 70, the first actuator 80, the second actuator 82, the first bladder assembly 90, the second bladder assembly 100, the vent unit 120, and/or the PEMF coil assembly 130. The method 170 may include sensing information (e.g., biomedical information, fatigue symptoms, etc.) of the user occupying the seat 30, via the sensor 70, such as to determine if the user exhibits signs/symptoms of fatigue and/or discomfort (step 174). If the user is in a state of fatigue (e.g., as determined by the ECU 50 and/or the sensor 70), the method 170 may include selectively activating one or more seat functions, such as the first actuator 80, the second actuator 82, the first bladder assembly 90, the second bladder assembly 100, the vent unit 120, and/or the PEMF coil assembly 130 to reduce fatigue symptoms exhibited by the user (see, e.g., FIGS. 4 and 5).

Figure 4:
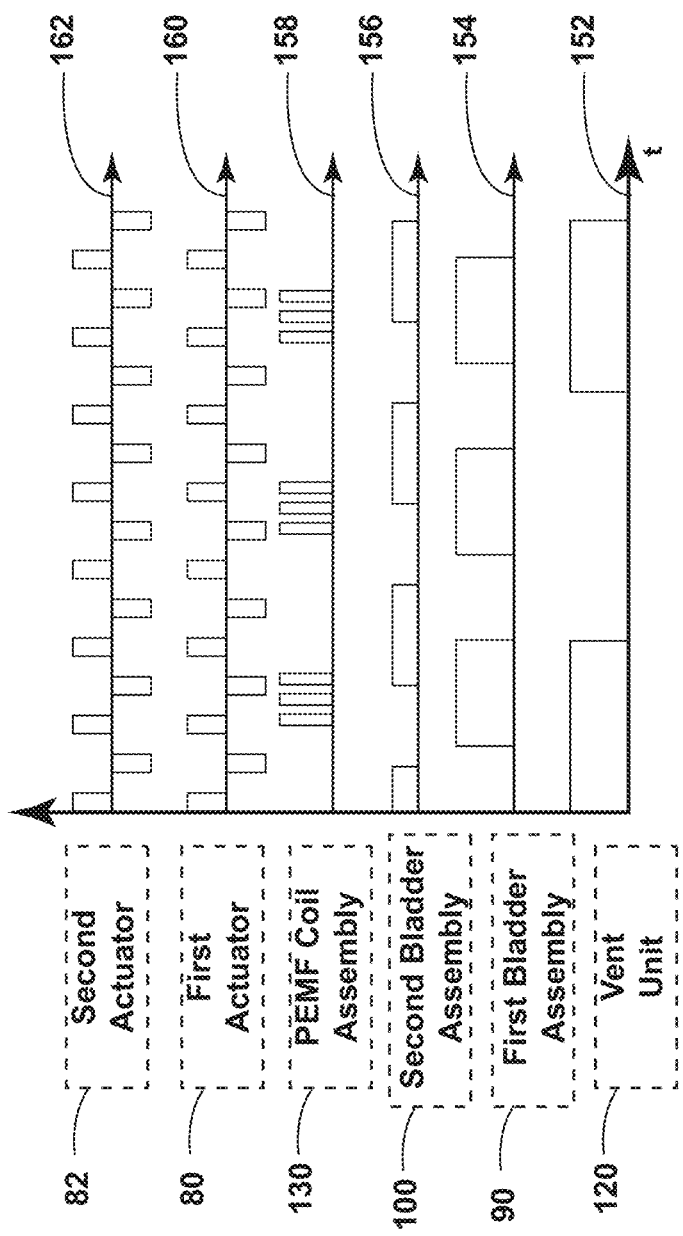
FIG. 4 is a graph generally illustrating an embodiment of operating a seat assembly according to teachings of the present disclosure.

With embodiments, the method 170 may include activating the vent unit 120, such as to reduce fatigue symptoms of the user (step 176). In embodiments, such as generally illustrated in FIG. 4, activating the vent unit 120 may include operating the vent unit 120 in the first mode for a first duration, such as about 4 minutes or more or less, and/or the second mode for a second duration, such as about 6 minutes or more or less (see, e.g., plot 152). Activating the vent unit 120 may include moving cool air to an area substantially proximate a neck/shoulder area of a user (e.g., which may trigger a diving reflex).

With embodiments, the method 170 may include actuating (e.g., automatically) the seat base 32 via the first actuator 80, and/or actuating the seat back 34 via the second actuator 82 (step 178), such as while the ECU 50 operates the vent unit 120 in the first mode. Activating the first actuator 80 may include rotating the seat base 32 from a first seat base position to a second seat base position in a first direction (e.g., upwards). The first seat base position and the second seat base position may be about 1 degree, or more or less, apart (e.g., angle β as shown in FIG. 1). The first actuator 80 may move the seat base 32 from the first seat base position to the second seat base position over a first duration, which may, for example and without limitation, be about seven seconds or more or less (see, e.g., first actuator plot 160 in FIG. 4). The ECU 50 may maintain the seat base 32 in the second seat base position for a second duration, which may, for example and without limitation, be about five seconds, or more or less. After the second duration, the ECU 50 control the first actuator 80 to rotate the seat base 32 from the second seat base position back to the first seat base position (e.g., in the second direction about 1 degree) over a third duration, which may, for example and without limitation, be about seven seconds (e.g., the third duration may be substantially the same as the first duration).

In embodiments, activating the second actuator 82 may include rotating the seat back 34 from a first seat back position to a second seat back position in a first direction (e.g., backwards), such as about 1.5 degrees or more or less (e.g., angle β in FIG. 1). The second actuator 82 may move the seat base 32 from the first seat back position to the second seat back position over a first duration, which may, for example and without limitation, be about seven seconds or more or less (see, e.g., second actuator plot 162 in FIG. 4). The ECU 50 may maintain the seat back 34 in the second seat back position for a second duration, which may, for example and without limitation, be about five seconds, or more or less. After the second duration, the ECU 50 control the second actuator 82 to rotate the seat back 34 from the second seat back position back to the first seat back position (e.g., in the second direction about 1 degree) over a third duration, which may, for example and without limitation, be about seven seconds (e.g., the third duration may be substantially the same as the first duration).

In some circumstances, the ECU 50 may move the seat base 32 and the seat back 34 from respective first positions to respective second positions at substantially the same time over substantially the same duration (e.g., a first duration), maintain second positions of the seat base 32 and the seat back 34 for the same duration (e.g., a second duration), and/or return the seat base 32 and the seat back 34 to respective first positions over the same duration (e.g., a third duration). In other circumstances, the seat base 32 and the seat back 34 may be operated at different times and/or for different durations. With embodiments, movement of the seat base 32 between the first and second seat base positions may be relatively subtle and/or may not, on its own, be intended to make the user more alert, but may shift the position of the user, at least to some degree, which may reduce discomfort.

In embodiments, the ECU 50 may operate the vent unit 120 in a cyclical mode for a venting duration, which may include multiple sets of the first vent unit duration, the second vent unit duration, and/or the third vent unit duration. The venting duration may, for example and without limitation, be at least twice as long as the first duration and the second duration combined.

Figure 5:
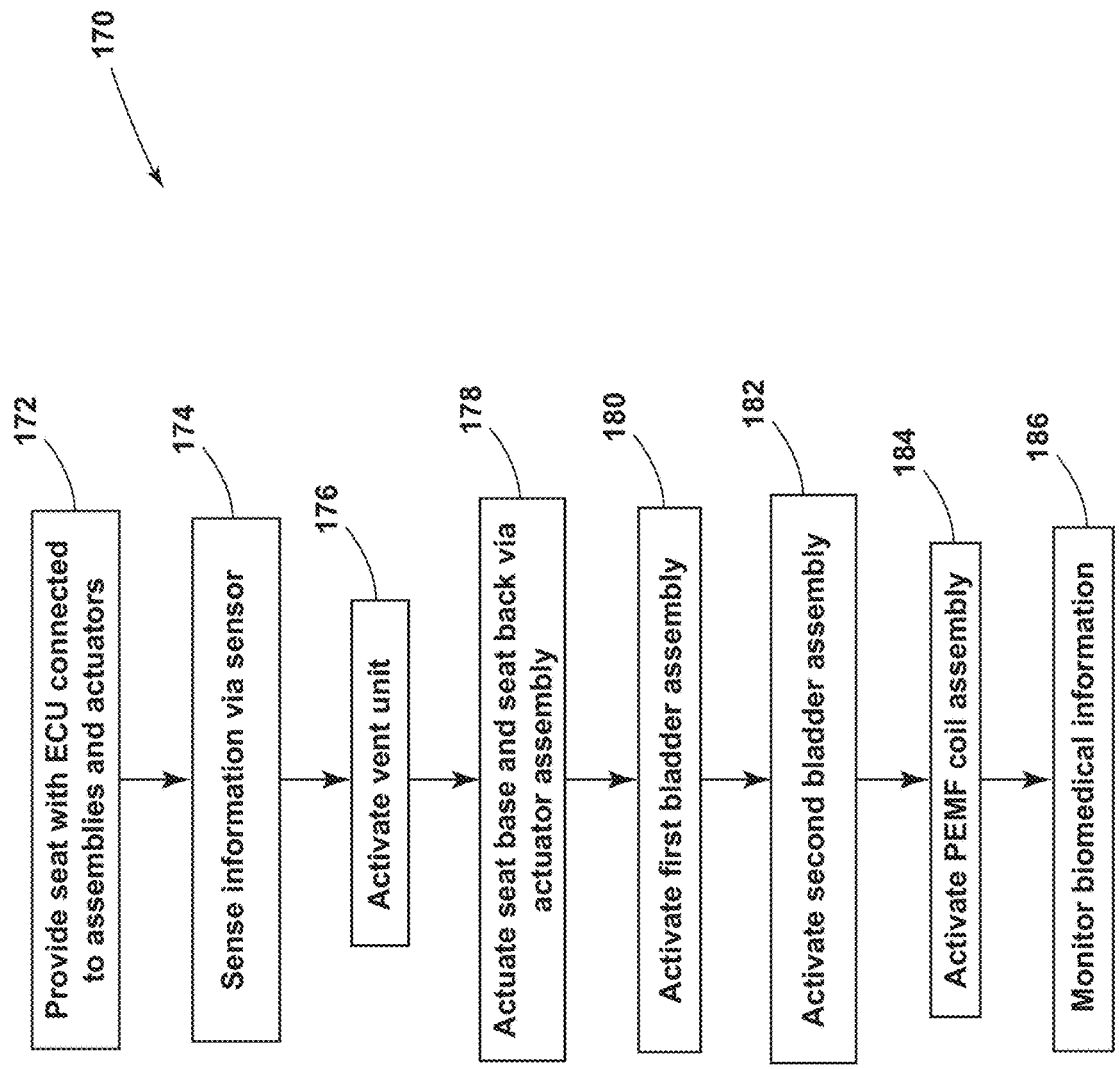
FIG. 5 is a flowchart generally illustrating an embodiment of a method of operating a seat assembly according to teachings of the present disclosure.

In embodiments, such as generally illustrated in FIGS. 4 and 5, the method 170 may include automatically activating the first bladder assembly 90 (step 180), such as while the ECU 50 operates the vent unit 120 in the first mode and/or the second mode. Activating the first bladder assembly 90 may include periodically/cyclically inflating and/or deflating the first bladder $92_1$, the second bladder $92_2$, the fifth bladder $92_5$, and/or the sixth bladder $92_6$ to massage a lumbar area and/or a shoulder area of the user (see, e.g., plot 154 in FIG. 4). The method 170 may include activating the second bladder assembly 100 (step 182), such as while the ECU 50 operates the vent unit 120 in the first mode and/or the second mode. Activating the second bladder assembly 100 may include periodically/cyclically inflating and/or deflating the bladder 102 of the second bladder assembly 100, such as to reposition the legs and/or hips of the user, at least to some degree, which may reduce fatigue symptoms and/or discomfort (see, e.g., plot 156 FIG. 4).

With embodiments, such as generally illustrated in FIGS. 4 and 5, the method 170 may include activating (e.g., automatically) a PEMF coil assembly 130 (step 184), such as while the ECU 50 operates the vent unit 120 in the first mode and/or the second mode. Activating the PEMF coil assembly 130 may include periodically supplying power to the first coil $132_1$, the second coil $132_2$, the third coil $132_3$, the fourth coil $132_4$, the fifth coil $132_5$, and/or the sixth coil $132_6$ (e.g., such as generally shown in plot 158 of FIG. 5) while the first bladder assembly 90 and/or the second bladder assembly 100 are activated. Activating the coils $132_N$ may reduce fatigue symptoms of the user associated with osteo-articular pain and/or inflammation.

In embodiments, the ECU 50 may monitor information of the user to determine if the user exhibits signs and/or symptoms of fatigue and/or discomfort, such as before, during, and/or after operating one or more seat functions (step 186). If the ECU 50 determines that fatigue/symptoms of the user were not sufficiently reduced via operation of one or more seat functions (e.g., the first actuator 80, the second actuator 82, the first bladder assembly 90, the second bladder assembly 100, the vent unit 120, and/or the PEMF coil assembly 130), the ECU 50 may continue to operate and/or cycle operation of one or more seat functions. If the ECU 50 determines that fatigue/symptoms of the user were sufficiently reduced (e.g., the user is fidgeting less, is more alert, etc.), the ECU 50 may deactivate some or all seat functions.

In examples, an ECU 50 may include an electronic controller and/or include an electronic processor, such as a programmable microprocessor and/or microcontroller. In embodiments, an ECU 50 may include, for example, an application specific integrated circuit (ASIC). An ECU 50 may include a central processing unit (CPU), a memory (e.g., a non-transitory computer-readable storage medium), and/or an input/output (I/O) interface. An ECU 50 may be configured to perform various functions, including those described in greater detail herein, with appropriate programming instructions and/or code embodied in software, hardware, and/or other medium. In embodiments, an ECU 50 may include a plurality of controllers. In embodiments, an ECU 50 may be connected to a display, such as a touchscreen display.

Various examples/embodiments are described herein for various apparatuses, systems, and/or methods. Numerous specific details are set forth to provide a thorough understanding of the overall structure, function, manufacture, and use of the examples/embodiments as described in the specification and illustrated in the accompanying drawings. It will be understood by those skilled in the art, however, that the examples/embodiments may be practiced without such specific details. In other instances, well-known operations, components, and elements have not been described in detail so as not to obscure the examples/embodiments described in the specification. Those of ordinary skill in the art will understand that the examples/embodiments described and illustrated herein are non-limiting examples, and thus it can be appreciated that the specific structural and functional details disclosed herein may be representative and do not necessarily limit the scope of the embodiments.

Reference throughout the specification to "examples, "in examples," "with examples," "various embodiments," "with embodiments," "in embodiments," or "an embodiment," or the like, means that a particular feature, structure, or characteristic described in connection with the example/embodiment is included in at least one embodiment. Thus, appearances of the phrases "examples, "in examples," "with examples," "in various embodiments," "with embodiments," "in embodiments," or "an embodiment," or the like, in places throughout the specification are not necessarily all referring to the same embodiment. Furthermore, the particular features, structures, or characteristics may be combined in any suitable manner in one or more examples/embodiments. Thus, the particular features, structures, or characteristics illustrated or described in connection with one embodiment/example may be combined, in whole or in part, with the features, structures, functions, and/or characteristics of one or more other embodiments/examples without limitation given that such combination is not illogical or non-functional. Moreover, many modifications may be made to adapt a particular situation or material to the teachings of the present disclosure without departing from the scope thereof.

It should be understood that references to a single element are not necessarily so limited and may include one or more of such element. Any directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of examples/embodiments.

Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. The use of "e.g." in the specification is to be construed broadly and is used to provide non-limiting examples of embodiments of the disclosure, and the disclosure is not limited to such examples. Uses of "and" and "or" are to be construed broadly (e.g., to be treated as "and/or"). For example and without limitation, uses of "and" do not necessarily require all elements or features listed, and uses of "or" are inclusive unless such a construction would be illogical.

While processes, systems, and methods may be described herein in connection with one or more steps in a particular sequence, it should be understood that such methods may be practiced with the steps in a different order, with certain steps performed simultaneously, with additional steps, and/or with certain described steps omitted.

All matter contained in the above description or shown in the accompanying drawings shall be interpreted as illustrative only and not limiting. Changes in detail or structure may be made without departing from the present disclosure.

It should be understood that an electronic control unit (ECU), a system, and/or a processor as described herein may include a conventional processing apparatus known in the art, which may be capable of executing preprogrammed instructions stored in an associated memory, all performing in accordance with the functionality described herein. To the extent that the methods described herein are embodied in software, the resulting software can be stored in an associated memory and can also constitute means for performing such methods. Such a system or processor may further be of the type having ROM, RAM, RAM and ROM, and/or a combination of non-volatile and volatile memory so that any software may be stored and yet allow storage and processing of dynamically produced data and/or signals.

It should be further understood that an article of manufacture in accordance with this disclosure may include a non-transitory computer-readable storage medium having a computer program encoded thereon for implementing logic and other functionality described herein. The computer program may include code to perform one or more of the methods disclosed herein. Such embodiments may be configured to execute via one or more processors, such as multiple processors that are integrated into a single system or are distributed over and connected together through a communications network, and the communications network may be wired and/or wireless. Code for implementing one or more of the features described in connection with one or more embodiments may, when executed by a processor, cause a plurality of transistors to change from a first state to a second state. A specific pattern of change (e.g., which transistors change state and which transistors do not), may be dictated, at least partially, by the logic and/or code.

What is claimed is:

1. A seat assembly, including:
a seat including a seat base and a seat back;
a sensor;
a vent unit disposed at least partially within the seat back; and
an electronic control unit (ECU) connected with the sensor and the vent unit;
wherein the ECU is configured to determine, via the sensor, if a user of the seat exhibits symptoms of fatigue;
the ECU is configured to operate the vent unit in a first mode and a second mode;
when the vent unit is in the first mode, the vent unit provides cool air to said user of the seat;
when the vent unit is in the second mode, the vent unit provides a lesser amount of cool air and/or air at a higher temperature than the cool air to said user of the seat; and
the ECU is configured to automatically switch the vent unit between the first mode and the second mode to reduce symptoms of fatigue of said user.

2. The seat assembly of claim 1, including a temperature sensor;
wherein the ECU is configured to communicate with the temperature sensor to determine an ambient temperature; and
the ECU is configured to control the vent unit such that a cool air temperature of the cool air is lower than the ambient temperature.

3. The seat assembly of claim 2, wherein the ambient temperature is a cabin temperature of a vehicle; and
the cool air temperature is at least about 7 degrees Celsius lower than the ambient temperature.

4. The seat assembly of claim 2, wherein the cool air temperature is about 15 degrees Celsius or lower.

5. The seat assembly of claim 1, wherein automatically operating the vent unit includes repeatedly operating the vent unit in the first mode for a first duration and operating the vent unit in the second mode for a second duration to maximize fatigue symptom reduction.

6. The seat assembly of claim 5, wherein the first duration is different than the second duration.

7. The seat assembly of claim 1, including a bladder assembly having one or more bladders disposed in the seat back;
wherein the ECU is configured to inflate and deflate the one or more bladders while the vent unit is in the first mode to reduce the fatigue symptoms of said user; and
the sensor includes a pressure sensor at least partially integrated with the bladder assembly.

8. The seat assembly of claim 7, including an additional bladder assembly having one or more additional bladders disposed in the seat base;
wherein the ECU is configured to inflate and deflate the one or more additional bladders of the additional bladder assembly while the vent unit is in the first mode to reduce the fatigue symptoms of said user.

9. The seat assembly of claim 1, including a first actuator connected with the seat base and a second actuator connected with the seat back;
wherein the ECU is configured to actuate the seat base via the first actuator and actuate the seat back via the second actuator; and
when the vent unit is in the first mode, the ECU is configured to automatically actuate the seat back from a first seat back position to a second seat back position over a first duration, maintain the second seat back position for a second duration, and return the seat back to the first seat back position after the second duration.

10. The seat assembly of claim 9, wherein a first angle between the first seat back position and the second seat back position is about 1.5 degrees.

11. The seat assembly of claim 10, wherein the ECU is configured to actuate the seat base from a first seat base position to a second seat base position during the first duration;
   a second angle between the first seat base position and the second seat base position is about 1 degree; and
   the first duration is longer than the second duration.

12. The seat assembly of claim 11, wherein the first duration is about four minutes and the second duration is about six minutes.

13. The seat assembly of claim 11, wherein symptoms of fatigue include one or more of user movements relative to the seat, reduced or irregular heart rate, reduced or irregular heart rate variability, and/or reduced or irregular blood pressure.

14. The seat assembly of claim 1, including a pulsed electromagnetic field (PEMF) coil assembly including at least one coil;
   wherein the ECU is configured to activate the at least one coil while the vent unit is in the first mode to reduce the fatigue symptoms of said user.

15. A seat assembly, including:
   a seat including a seat base, a seat back, and a headrest;
   a bladder assembly disposed at least partially in the seat;
   a biomedical sensor configured to sense biomedical information of a user of the seat, the biomedical sensor at least partially integrated with the bladder assembly;
   an actuator assembly configured to control a position of the seat base and/or the seat back;
   a vent unit disposed at least partially within the seat back and including a portion disposed proximate the headrest;
   a PEMF coil assembly disposed at least partially in the seat back; and
   an ECU configured to control the actuator assembly, the bladder assembly, the vent unit, and the PEMF coil assembly;
   wherein the ECU is configured to determine if the user of the seat exhibits symptoms of fatigue via the biomedical sensor;
   the ECU is configured to automatically operate the vent unit in a first mode and a second mode in an alternating configuration to reduce the fatigue symptoms of said user;
   when the vent unit is in the first mode, the vent unit provides cool air to an area proximate a neck of said user;
   when the vent unit is in the second mode, the vent unit provides a lesser amount of cool air and/or provides air at a higher temperature than the cool air; and
   the ECU is configured to automatically activate the actuator assembly, the bladder assembly, and the PEMF coil assembly when the vent unit is in the first mode to reduce the fatigue symptoms of said user.

16. A method of operating a seat assembly including a seat, a biomedical sensor, a vent unit, and an ECU connected with the biomedical sensor and the vent unit, the method including:
   sensing, via the biomedical sensor, if a user of the seat exhibits symptoms of fatigue; and
   automatically operating the vent unit in a first mode for a first duration and in a second mode for a second duration to reduce symptoms of fatigue of said user;
   wherein when the vent unit is in the first mode, the vent unit supplies cool air to said user; and
   when the vent unit is in the second mode, the vent unit provides a lesser amount of cool air and/or provides air at a higher temperature than the cool air.

17. The method of claim 16, wherein automatically operating the vent unit includes alternating between the first mode and the second mode for a venting duration to maximize an effectiveness of the vent unit for reducing symptoms of fatigue.

18. The method of claim 17, wherein the first duration is less than the second duration; and
   the venting duration is at least twice as long as the first duration and the second duration combined.

19. The method of claim 16, wherein the cool air includes a temperate that is at least about 7 degrees cooler than a cabin temperature and is about 15 degrees Celsius or lower.

20. The method of claim 16, including automatically operating an actuator assembly, a bladder assembly, and a coil assembly to reduce the symptoms of fatigue of the user while automatically operating the vent unit.

* * * * *